United States Patent [19]

Normann

[11] Patent Number: 4,522,194
[45] Date of Patent: Jun. 11, 1985

[54] METHOD AND AN APPARATUS FOR INTRA-AORTIC BALLOON MONITORING AND LEAK DETECTION

[75] Inventor: Nils A. Normann, Houston, Tex.

[73] Assignee: Baylor College of Medicine, Houston, Tex.

[21] Appl. No.: 503,117

[22] Filed: Jun. 10, 1983

Related U.S. Application Data

[63] Continuation-in-part of Ser. No. 467,623, Feb. 18, 1983, abandoned.

[51] Int. Cl.³ ............................................... A61B 5/00
[52] U.S. Cl. ..................................................... 128/1 D
[58] Field of Search ............... 128/1 D, 693, 720, 734, 128/908; 324/61 R; 604/97–99

[56] References Cited

U.S. PATENT DOCUMENTS

| | | | |
|---|---|---|---|
| 2,661,734 | 12/1953 | Holzer et al. | 128/734 |
| 3,690,313 | 9/1972 | Weppner et al. | 128/908 |
| 3,698,381 | 10/1972 | Federico et al. | 128/1 D |
| 3,750,649 | 8/1973 | Severinghaus | 128/734 |
| 3,974,825 | 8/1976 | Normann | 128/1 D |
| 4,088,125 | 5/1978 | Forgione et al. | 128/734 |
| 4,215,698 | 8/1980 | Nuwayser | 128/734 |
| 4,300,574 | 11/1981 | Briggs | 128/734 |
| 4,327,709 | 5/1982 | Hanson et al. | 128/1 D |

Primary Examiner—William E. Kamm
Attorney, Agent, or Firm—Fulbright & Jaworski

[57] ABSTRACT

A method of and an apparatus for intra-aortic balloon monitoring and leak detection in which the balloon is inserted into the aorta of a body and the balloon is inflated and deflated with gas by a control system and in which the balloon includes an electrical conductor therein extending out of the body. An alternating current source is applied between the electrical conductor and an electrode connected to the exterior surface of the body thereby transmitting an alternating current through the body and across the balloon. The impedance between the electrical conductor and the electrode is measured which is an indication of the inflation and deflation of the balloon and the occurrence of any leak in the balloon. The control system of the balloon is automatically shut down in the event the impedance falls below a predetermined level. The frequency of the alternating current is above the range of cardiac susceptibility and the magnitude of the electrical current passing through the body is small and limited. Safety is further ensured by a high degree of electrical isolation of electronic circuitry in contact with the body. Under appropriate circumstances, the electrical method for balloon leak detection can be implemented also by the employment of direct current and the measurement of conductance change caused by a balloon defect.

19 Claims, 9 Drawing Figures

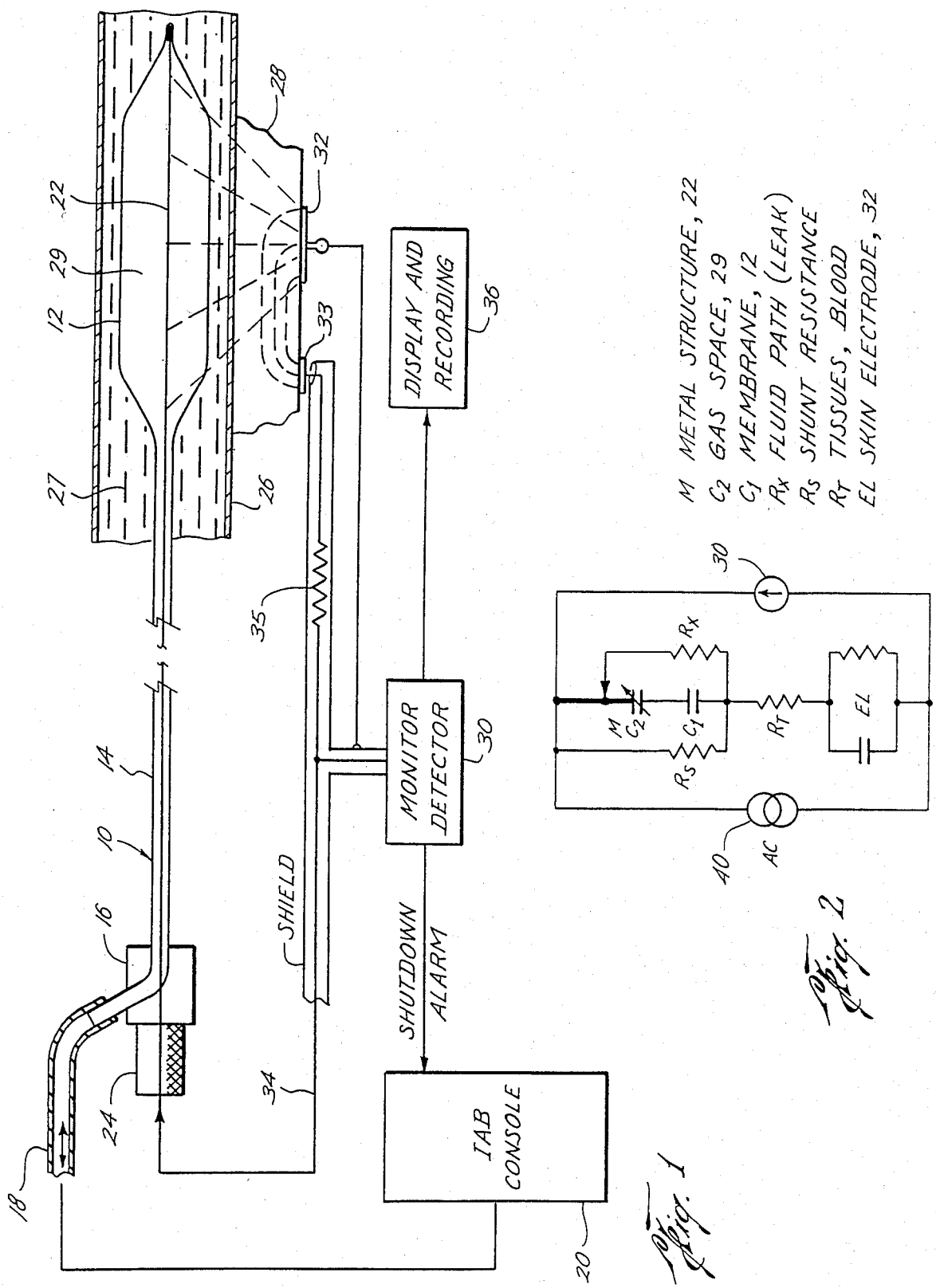

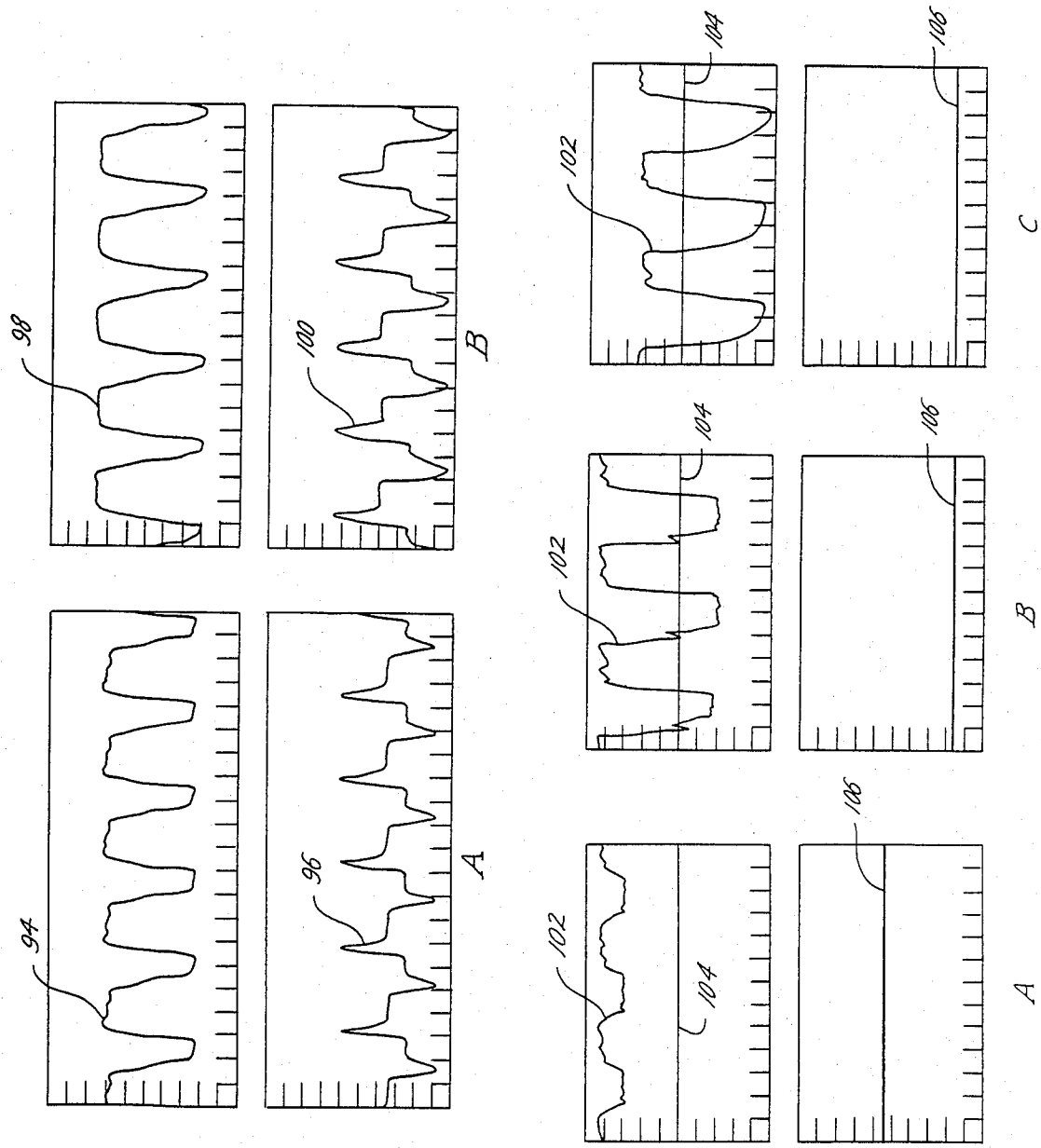

METHOD AND AN APPARATUS FOR INTRA-AORTIC BALLOON MONITORING AND LEAK DETECTION

CROSS-REFERENCE TO RELATED APPLICATIONS

This application is a continuation-in-part of my copending application Ser. No. 467,623, filed Feb. 18, 1983 now abandoned.

BACKGROUND OF THE INVENTION

The employment of gas activated intra-aortic balloons is at the present time an accepted therapeutic method for mechanically assisting the heart. The balloon is inserted into the proximal portion of the descending thoracic aorta and is inflated and deflated with gas in synchoronism with heart action. Therapeutic benefit is derived from decreasing the workload of the heart and from augmenting perfusion of the coronary arteries during diastole. The number of applications, in the United States alone, is in excess of 18,000 per year. With the advent of the so-called "percutaneous" type balloon, the membrane of the balloon is significantly thinner than in the older types. This thinness and the necessity of wrapping the balloon by winding it up on itself for percutaneous insertion and thereafter unwinding it in the aorta have increased the risks of balloon failure caused by any weaknesses introduced during manufacture, by damage caused by intra-aortic plaques, or by inappropriate medical techniques. However, a balloon failure such as a leak, and in particular a rupture, which allows the inflating gas to enter the bloodstream, can cause a disastrous gas embolism. The prior art, the detection means, which are incorporated into existing intra-aortic balloon drive and control systems, are based on detecting with varying degrees of sensitivity—a loss of drive gas, i.e., after gas has escaped. Equally unsatisfactory is "detection" by personnel observing blood appearing in the pneumatic drive line.

The present invention is directed to a method of and an apparatus for providing a direct, intra-corporeal detection of intra-aortic balloon leaks which when used in conjunction with an automatic shutdown and an alarm system is designed to prevent gas escape and consequent gas embolism. In addition, the present method and apparatus also provides the means for direct monitoring of the inflation and deflation of the balloon operation, a feature presently not available in balloon drive systems.

SUMMARY

The present invention is directed to a method of and an apparatus for intra-aortic balloon monitoring and leak detection. One object is to provide a method and apparatus for a direct sensitive detection of balloon failure and for a consequent automatic shutdown and an alarm. The present apparatus and method is based upon the continuous, on-line measurement, preferably by means of an alternating current, although direct current may be used, the electrical impedance across the balloon membrane thereby providing a signal for automatic shutdown when the measured impedance is reduced below a predetermined level by the shunting effect of a transmembrane fluid conduction path. A further object is the provision of using an alternating current impedance measurement of the balloon to monitor the inflation and deflation of the intact balloon.

A still further object of the present invention is the provision of a method of and an apparatus for monitoring the operation and detection of leaks of an intra-aortic balloon inserted into the aorta of a body in which the balloon includes internally an electrical conductor that is accessible outside the body. The method includes attaching an electrode to the exterior surface of the body and applying an alternating current source between the electrical conductor and the electrode, thereby transmitting an alternating current through the body and across the balloon. An impedance measuring means is electrically connected to the electrode and the electrical conductor for measuring the impedance across the balloon membrane and the impedance between balloon membrane and the electrical conductor. As the intact balloon is expanded and contracted the impedance across the gas space will change, and balloon membrane position and motion can thus be monitored.

A still further object of the present invention is the provision of a shutdown means connected to the impedance measuring means for automatically stopping the operation of the balloon when the impedance falls below a predetermined level. In the event of a leak or rupture in the membrane of the balloon, the resulting transmembrane fluid path, between the blood outside the balloon and the electrical conductor inside the balloon, will reduce the measured impedance and thereby, by means of appropriate circuitry, trigger automatic shutdown and alarm. Thus, escape of gas into the bloodstream will in most cases be prevented.

A still further object of the present invention is the provision of a signal means connected to the measuring means for actuating a signal when the impedance exceeds a predetermined level which is an indication that the electrical measuring circuit is improperly operating such as would occur if the external electrode was not making a good contact with the body.

Still a further object of the present invention is the improvements of various safety means including means for limiting the electrical current flowing between the electrode and the electrical conductor and passing through the body and wherein the alternating current is sinusoidal and wherein the frequency of the alternating current is above the range of cardiac susceptibility.

Still a further object of the present invention is the provision of a method and apparatus for monitoring the operation of and detecting a leak in an intra-aortic balloon inserted into the aorta of a body in which the balloon is inflated and deflated with gas by a control system and in which the balloon includes an electrical conductor therein which extends or can be extended out of the body and which includes an electrode or electrode assembly adapted to be affixed to the exterior of the body. An electrical subassembly including an alternating current impedance measuring circuit is connected to the external electrode(s) and the internal electrical conductor for providing a current path through the body across the balloon. The subassembly is powered with direct current from an electrically isolated power source. A sinusoidal oscillator provides an alternating current signal to the measuring circuit but is isolated from the subassembly by a first transformer. An alternating current to direct current converter is connected to the output of the measuring circuit but is isolated from the subassembly by a second transformer.

A signal processor is connected to the output of the converter for providing an output proportional to the measured impedance and the output of the processor is connected to the gas control system for deactivating the control system when the measured impedance falls below a predetermined level.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIG. 1 is a schematic elevational view of a conventional intra-aortic balloon system in use with the present invention, FIG. 2 is a schematic representing in analog form the electrical characteristics of the system being measured.

DESCRIPTION OF THE PREFERRED EMBODIMENT

Figure 3:
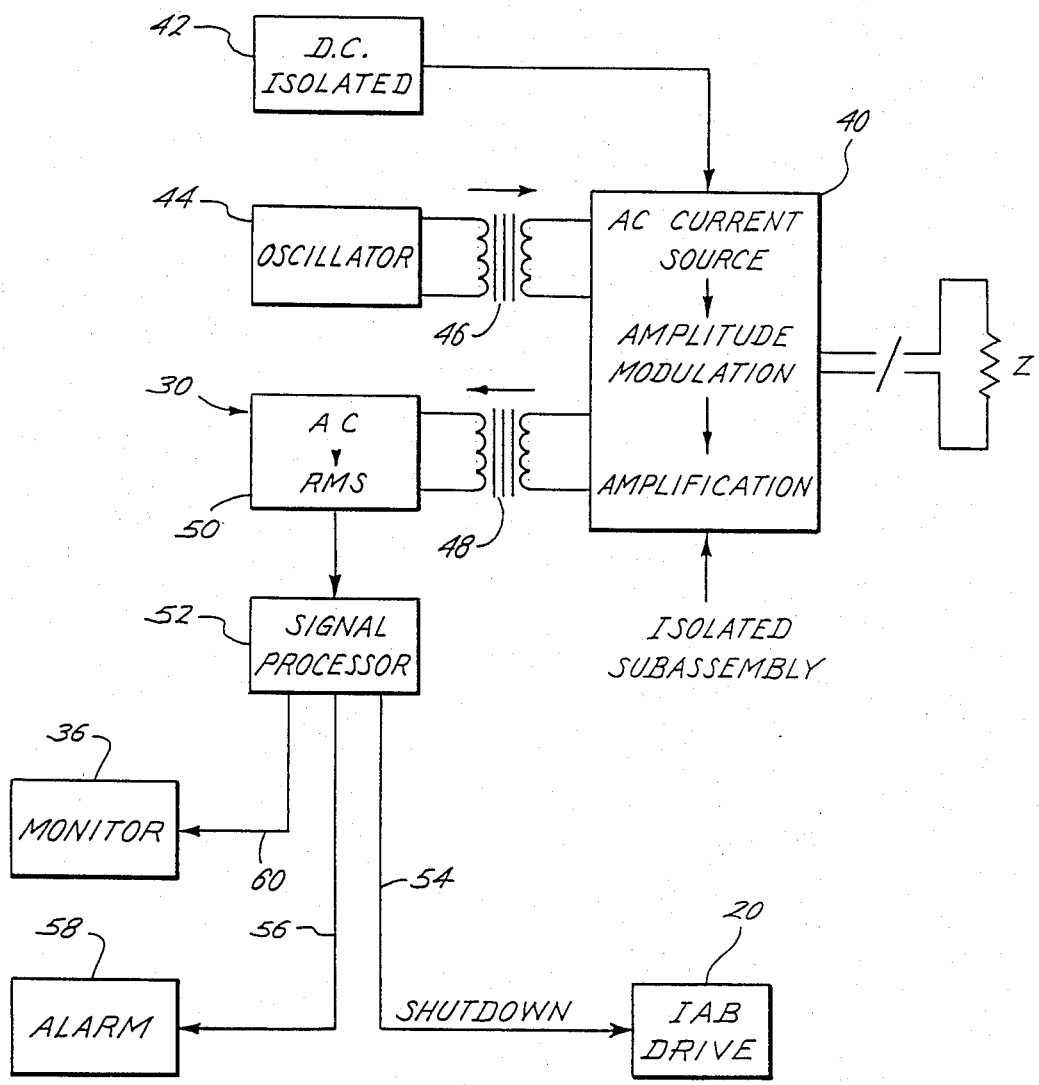
FIG. 3 is a block diagram of the principal features of the electronic design employed in implementation of the present invention.

Referring now to the drawings, and particularly to FIG. 1, the reference numeral 10 generally indicates a conventional intra-aortic balloon system in combination with the monitoring and leak detection system of the present invention, generally indicated by the reference numeral 30 of the present invention. The system 10 generally includes a flexible balloon 12 mounted on a catheter 14 which is connected to a handle 16 and is also in communication with a gas line 18 which in turn is connected to the control system 20. The balloon 12 is also supported by a metal rod 22 which is rotatably attached to the handle 16 and affixed to turning knob 24. In use, the knob 24 is rotated to wrap the balloon 12 around the rod 22 to form it into a compact roll for insertion through a prepositioned 4 mm ID sleeve into the aorta 26 in a body 128. After the balloon 12 is inserted into the aorta 26, it is unwrapped by reversing the rotation of the turning knob 24. The control system 20 then transmits gas to and from the balloon 12 through the line 18 and catheter 14. The cycling is precisely synchronized with the heart action whereby the balloon assists the heart. However, the balloon 12 is a thin membrane and is subject to wear and tear by twisting it into a roll, inserting it, unrolling it, and continuously inflating and deflating it wherewith repeated contact with a calcified plaque protruding from the aortic wall may cause localized membrane damage. A leak or rupture in the balloon 12 could lead to disastrous consequences as the gas in the balloon could escape into the blood 27 in the aorta 26 and thus create gas embolism in the patient.

The present invention is directed to monitoring the operation of the balloon 12 and the detection of any leak therein by measuring the impedance across the balloon membrane 12 and the gas space 29 between the membrane 12 and the metal rod 22. The impedance measurement is made practical by using the metal rod 22, which is normally incorporated for the purpose of supporting the balloon 12 and controlling the wrapping and unwrapping of the balloon 12, as an electrical electrode. The metal rod 22 provides the means for passing an alternating current across the balloon membrane 12 while the balloon 12 is in the aorta 26 in the body 28. The current path is provided by affixing a skin electrode 32 to the exterior of the body 28 and passing the current through the body tissues and fluids, blood, across the balloon membrane 12 and gas space 29, and then via the metal conductor 22 back to the current source. Thus, the present invention 30 includes an alternating current source which is connected to an electrode 32 affixed to the human body and by a conductor 34 to the electrical conductor 22 incorporated in knob 24.

Monitoring of the operation of the balloon 12 and the detection of a transmembrane defect are accomplished by measuring the impedance by means of an electrically isolated (floating) constant current source which is connected to the electrode 32, such as a silver-silver-chloride skin electrode, and to the metal conductor 22 by the electrical conductor 34. Since the impedances of the electrode 32 interface, tissues and blood of the body 28 are relatively low, the main impedances are those across the balloon membrane 12 and across the gas space 29. That is, in effect, the measured impedance is of two in-series capacitors of which one, that of the membrane 12, is for practical purposes constant. The various components which make up the overall impedance Z are shown in analog form in FIG. 2 in which an alternating current from source 40 is applied between the electrode 32 and the electrical conductor 22. While the total impedance Z consists of the various listed factors, the main variable factors may be used to monitor the operation of the intact balloon 12 as well as to detect a membrane leak or rupture. For example, the variation in the total capacitance across the balloon is approximately 200 pf as a standard 40 cc balloon is inflated and deflated. With the high impedance across the membrane 12 and the gas space 29, even a minute defect in the membrane 12, causing a tiny fluid channel across the membrane 12, can easily be detected by the appearance of the factor $R_x$. The present invention utilizes a drop in the measured impedance Z, such as when the blood 27 makes contact with the electrical conductor 22 during balloon deflation, to trigger an alarm and an immediate shutdown of the control system 20 of the balloon 12. Extensive benchtop testing, under conditions analogous to those encountered clinically, has demonstrated that a pin hole defect in the membrane 12 can be detected before any gas escapes. A very dangerous balloon failure, that can occur, is a partial detachment of the balloon 12 from the catheter 14 during insertion, an event that could lead to the disastrous consequences of 40 cc of gas being pumped into the bloodstream 27. However, the present invention, by measuring the lowering of the impedance between the electrode 32 and the electrical conductor rod 22, has the capability of triggering an immediate shutdown and thus preventing even a single inflation cycle.

The intra-aortic balloon system 10 shown in FIG. 1 is a type exemplified by the "Percor 10.5 F" model from the Datascope Corporation. However, the present invention is applicable to various other types of intra-aortic balloon models. In the device of FIG. 1, the metal rod 22 is a thin solid wire which is normally electrically insulated by the balloon 12 from the blood 27 in the aorta 26. In another conventional system, sold by Kontron Corporation, the metal conductor consists of a small caliber stainless steel tubing, the lumen of which communicates with blood at the end of the balloon for permitting balloon insertion directly over a guide-wire, blood pressure measurement and intra-aortic injections. However, for ease of insertion, a flexible hollow 5 centimeter long segment is at the distal end of the balloon. Since this flexible segment is electrically insulated, the impedance of the inside fluid column (saline perfusate) is high enough, approximately 30 Kohm (cf. $R_s$ in FIG. 2), to make the present system 30 applicable. In invitro experiments with this "dual lumen" type balloon, the balloon inflation and deflation pattern was readily discernible and with the appropriate threshold setting, a small pin hole in the balloon membrane, equivalent to a $R_x$ of about 50 Kohm, was readily detected.

The monitoring of balloon operation and the detection of a balloon membrane leak are effective for balloons with and without the second lumen. The sensitivity of detection of increased impedance, caused typically by poor contact of the external electrode 32, is straightforward with the dual lumen type, but is, however, low for balloons 12 containing only the pneumatic channel, as depicted in FIG. 1. In conjunction with the latter type of balloon 12, the sensing of an impedance increase is significantly improved by introducing a second external electrode 33 which, via a 30 Kohm resistor 35 (cf. $R_s$ in FIG. 2) is connected to the internal conductor lead 34. As presented schematically in FIG. 1, by this arrangement a portion of the alternating current will flow through the thus created shunt, and an increase in impedance caused by poor continuity of electrodes, connectors or leads, can readily be detected. Additionally, since 30 Kohm matches the effective resistance of the fluid shunt in the dual lumen balloon (Kontron), uniformity of signal amplitude is attained.

Impedance and changes thereof may be measured in a number of ways. However, in making electrical measurements on the human body, important system specifications are safety, efficacy, reliability and ease of clinical implementation. In the present system 30, safety is ensured (1) by using a sinusoidal alternating current signal with a frequency beyond the range of cardiac susceptibility, for example at a frequency of 10 KHz or higher, (2) by limiting the current passing through the human body, for example by limiting the current to 10 microamperes, (3) by providing a high degree of electrical isolation, particularly from power ground, and (4) by excluding possibilities of interference with the normal operation of the balloon system 10. While passing an electrical current through the human body for the measurement of impedance is used clinically for other purposes and in different configurations, the present purpose, method and configuration are novel.

Referring now to FIG. 3, a block diagram of the present system 30 is best seen connected to the control system 20 of the intra-aortic balloon system 10. One feature of the system 30 is the electrical isolation of the subassembly 40 which contains the electronic components connected to the body 28 of the patient. For safety reasons, the subassembly 40 incorporates a minimum of total circuitry. The circuitry in the subassembly 40 is powered by means of an isolation dc to dc converter 42. If desired, the subassembly 40 could be battery powered for further isolation. The alternating current signal is provided by a conventional oscillator 44 which is coupled by a first transformer 46 to the isolated subassembly 40. The impedance (amplitude) modulated signal from the isolated subassembly is coupled by a second transformer 48, and is tranmitted to an ac to dc rms converter 50. If desired, optical coupling could be substituted for the transformers 46 and 48. The resulting dc voltage, which corresponds to the amplitude (rms) of the impedance measuring ac signal, is then transmitted to a signal processor 52 for providing an automatic shutdown signal 54 to the balloon control system 20, a signal 56 to an alarm output 58 and a signal 60 to a monitor and/or recorder 36. It is noted that patient 28 is by means of subassembly 40 isolated from main circuit components and earth ground. Preferably, electrical power is applied to and discontinued from the human body 28 gradually.

Figure 4:
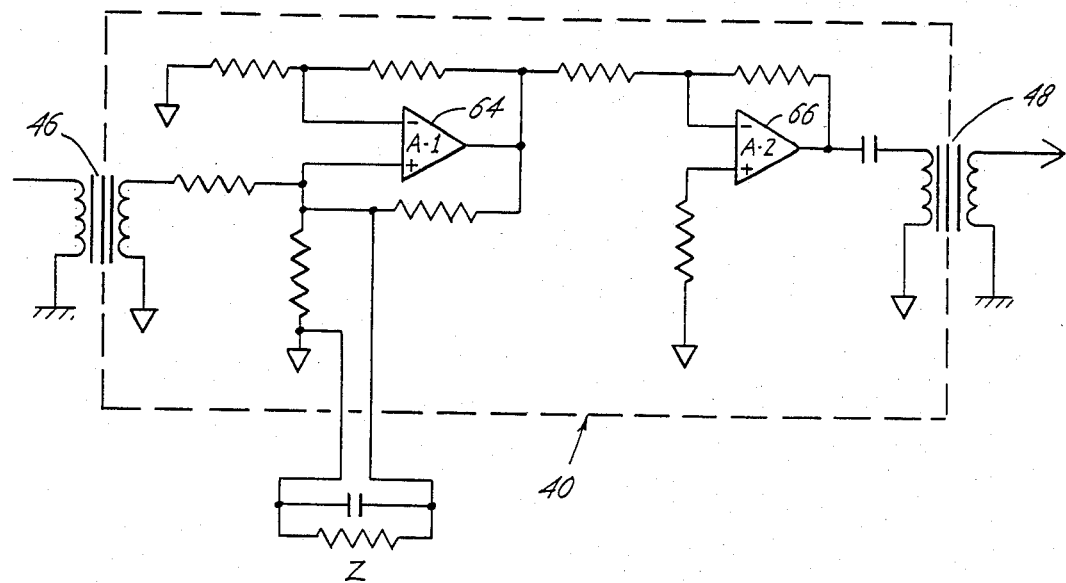
FIG. 4 is a schematic of the impedance measuring circuit of the present invention.

Referring now to FIG. 4, a schematic diagram of the circuitry of the subassembly 40 is best seen. A first amplifier 64 is arranged in a Howland configuration for receiving the ac signal through the transformer 46 and for providing a constant, alternating current through the circuit ground referenced measured impedance Z without any dc component. Output from the first amplifier 64 is amplified by a second amplifier 66 and transmitted through the transformer 48 to the ac to dc converter 50 (FIG. 3).

Figure 5:
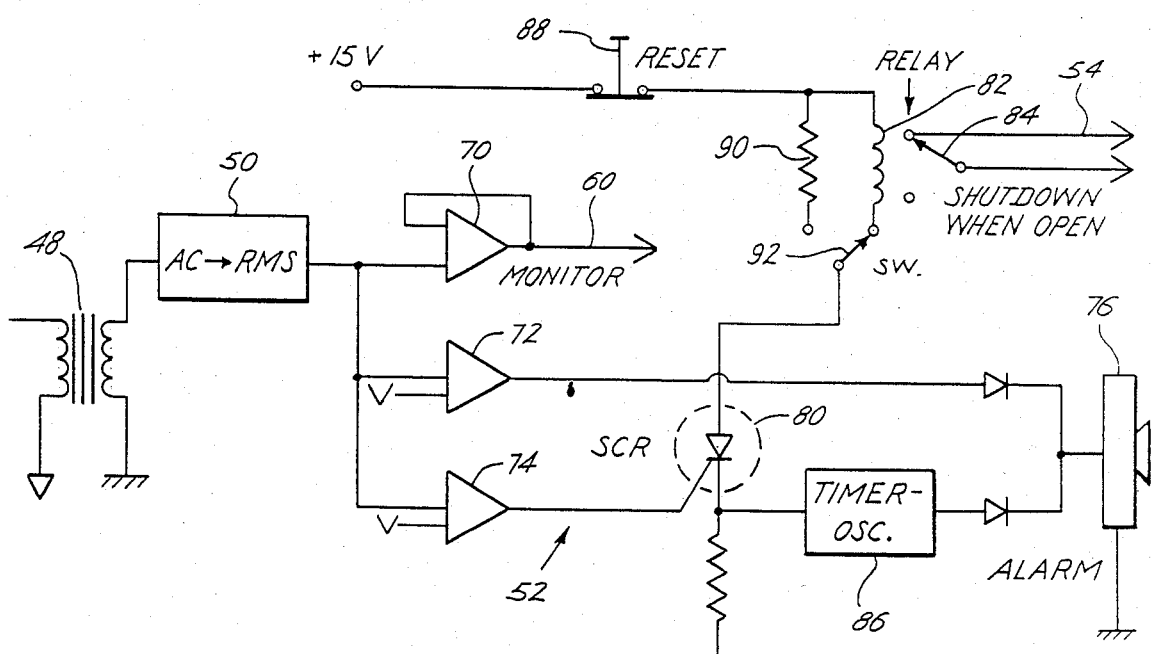
FIG. 5 is a block diagram of the monitor output and the shutdown and alarm circuitry of the present invention, FIG. 6 includes graphs A and B illustrating the output measurement of the impedance change as a function of balloon operation for different balloon filling volumes, FIG. 7 includes output graphs A, B and C illustrating impedance changes caused by a small membrane leak and the consequently triggered shutdown signal.

The signal processor is best seen in the simplified block diagram in FIG. 5. The processor 52 receives the impedance measuring signal through the transformer 48 and converts the ac signal to its rms dc equivalent in converter 50. The dc signal is transmitted to a buffer amplifier 70 to provide a signal on line 60 to any suitable monitor or recorder 36 (FIG. 3). The incoming dc signal which is used for monitoring the balloon operation is fed into a first comparator 72 and a second comparator 74. The first comparator 72 is triggered when the dc level exceeds a preset reference level, as may be caused by the patient lead or electrode 32 malfunction which causes an increase in the measured impedance. Comparator 74 is triggered when the dc level falls below a preset reference level such as caused by a leak in the balloon membrane 12 creating a fluid conductive path across the balloon membrane 12 causing a decrease in the measured impedance. Actuation of the first comparator 72 is transmitted to an alarm 76 such as a visual or an audible alarm. However, actuation of the second comparator 74 triggers a latching circuit such as provided by a silicon controlled rectifier (SCR) 80 which in turn causes a current to flow through a coil 82 of a relay for opening a normally closed switch 84 of the relay which shuts down the control system 20 (FIG. 3) which operates the balloon. Simultaneously, current through the SCR 80 enables a timer oscillator 86 which provides an interrupted sounding alarm 76 and a flashing light. The SCR 80 has the desirable feature of having an inherent latching property. That is, the latch 80 remains ON even if the original trigger signal from the comparator 74 is removed from the gate of the SCR. Consequently, a resumption of the balloon 12 operation requires a reset action on the part of the human operator by actuating the reset switch 88. The SCR 80 may be connected to a substitute resistor 90, with a switch 92, for allowing the system to be tested without interrupting the operation of the balloon 12.

During normal pumping with the intact balloon 12, the inflation and deflation of the balloon 12 may be monitored as it is reflected in the dc output from the converter 50. The tracings reproduced in FIG. 6 illustrate the correlation of the balloon sensing output with the pressure variations in the drive gas line to the balloon 12. In FIG. 6 the tracing 94 illustrates the impedance change across the balloon 12 as a function of balloon operation while the lower tracing 96 indicates the line pressure of the gas actuating the balloon. It is to be noted that as the gas pressure increases and the balloon 12 is inflated, the impedance across the balloon increases. In FIG. 6 in the graphs A the 40 cc balloon was inflated only partially with 25 cc of gas. Similar tracings are provided in FIG. 6 in the graphs B wherein tracing 98 indicates the impedance change as a function of balloon operation and tracing 100 indicates the gas line pressure. However, in the graphs B of FIG. 6 the balloon was fully inflated with 40 cc of gas. By means of appropriate circuitry, the monitored output may be linearized for attaining proportionality with balloon volume.

FIG. 7 includes graphs A, B and C which are tracings of the measured impedance reading 102 relative to a shutdown level of 104 and a tracing of the shutdown signal 106. In to graph A of FIG. 7 the tracings illustrate normal balloon operation wherein the impedance tracing 102 is at all times above the predetermined reference 104. In graph B a small puncture has occurred in the membrane of the balloon 12 causing the impedance value 102 to fall, during balloon deflation, below the predetermined set value 104 and consequently causing the shutdown signal 106 to fall to a shutdown value (as it appears at the anode of the SCR). In continous operation in graph C, after some fluid (saline) had accumulated in the balloon 12 through the small puncture, causing the measured impedance to be reduced even during balloon inflation.

As indicated above, it is the preferred embodiment of the present invention to utilize alternating current which can both determine a balloon leak and monitor the static and dynamic characteristics of the balloon operation. However, under certain circumstances, if leak detection is the sole objective, then this may be accomplished, in principle, by utilizing a direct current (dc). For example, referring to FIG. 1, a dc source may be connected to a reference skin electrode such as electrode 32 and to the electrical metal conductor 22 within the balloon 12. As long as the balloon 12 is intact, no electrical current will flow since the balloon 12 and catheter 14 will represent, for practical purposes, an infinite resistance to direct current. If, however, a leak develops, typically across the membrane of the balloon 12 or its attachment to the catheter 14, then a fluid conductive path is established that permits a measurable current to flow, typically, when the balloon is deflated. Thus, an electrical signal is obtained which can be similarly utilized for alarm and automatic shutdown as previously described.

In the "dual lumen" type of intra-aortic balloon, as described on pages 8 and 9, the incorporation of a fluid channel constitutes in effect an electrical shunt relative to the balloon membrane. In this case, a current is flowing through the shunt and the measurement is likely to be affected by the problems associated with the use of dc under the circumstances concerned. Phenomena, such as electrical polarization and galvanic potentials are likely to be present and may vary considerably with changes at the electrode interfaces, typically as caused by electrode motions. Consequently, the dc detection of a balloon membrane leak, particularly a small one, would be significantly degraded by the extraneous potentials and, therefore, the use of dc measurements with the "dual lumen" type of balloon is inferior to measurements with alternating current.

In short, the employment of an alternating current is the preferred method as it permits continuous on-line monitoring of balloon operation and provides sensitive and reliable detection of intra-aortic balloon leaks, regardless of whether the balloon has a fluid channel or not. However, in fulfilling the sole objective of leak detection in a "single lumen" balloon, the direct current method may be employed. Since under these circumstances no current will flow across the intact balloon, the dc approach lends itself for a sensing system design that permits long-term battery operation. Furthermore, if desired, a dc sensing module may advantageously incorporate a wireless transmitter which, similarly, is activated and powered only during testing and in response to a balloon leak.

Safety requirements are similar to those pertaining to the use of alternating current, as previously stated. Patient connected circuitry needs to be isolated from earth ground; in the system here described, isolation is achieved by means of battery operation combined with optical coupler interfacing (alternatively telemetry). Further, if a balloon leak should occur, the direct current flowing through the body should be limited (for instance a constant current of 10 to 20 microamp.) and its onset should be gradual.

Figure 8:
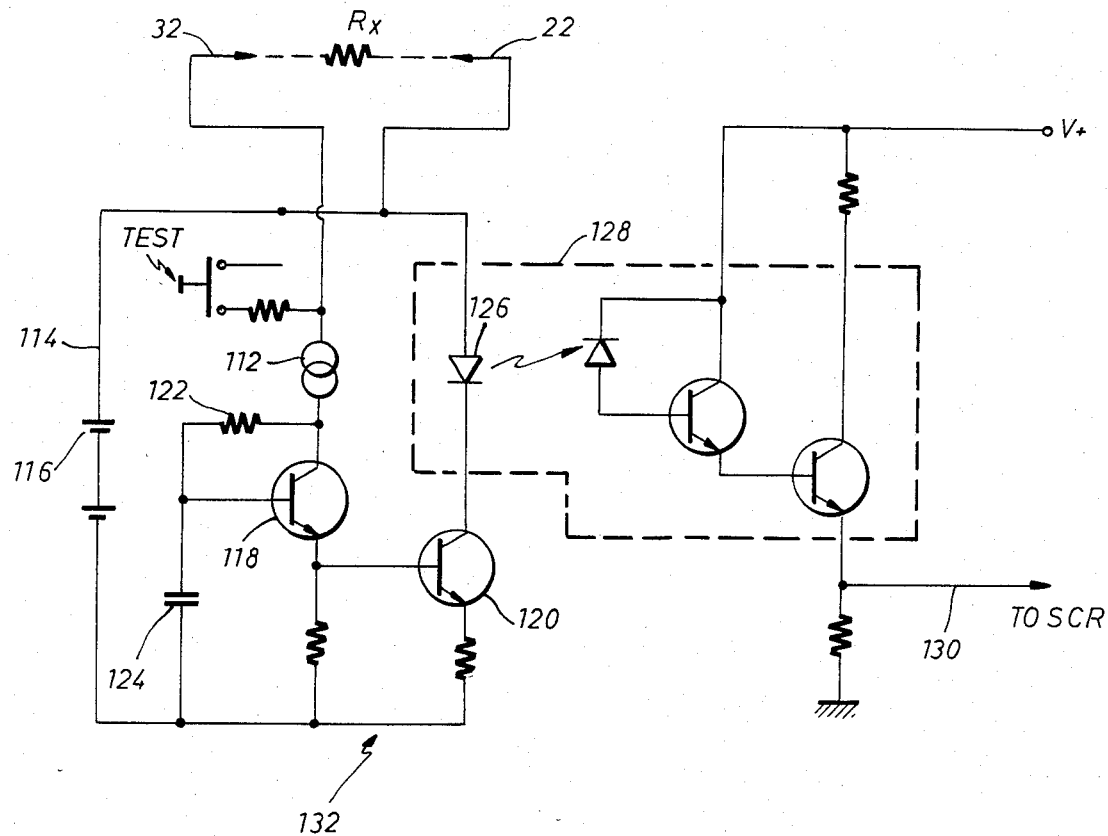
FIG. 8 is an elevational schematic of a direct current sensing circuit.

Referring now to FIG. 8, an electronic circuit implementation is shown. In this design, a reference skin electrode 32 and the intra-balloon conductor 22 are connected between the positive side of a constant current source 112 and the plus side 114 of the battery 116. Thus, with an intact balloon no dc flows through transistor 118 and transistor 120 is consequently biased in the non-conducting state. Should a balloon membrane leak occur, an electrical conduction path from 114 to 112 is established, as symbolized by $R_x$. Via the constant current source, current flows through resistor 122 and builds up a charge on capacitor 124 and thus a gradual onset of conduction through transistor 118 is effected. This in turn activates transistor 120 and the LED 126 in the optical coupler 128, resulting in a coupler output signal 130 for triggering a latching silicon controlled rectifier (SRC) such as the SRC 80 in FIG. 5. In this circuit, in the standby non-triggered mode, the current through transistor 120 is one to two nanoamp.; alternately, an FET may be used. Because of the negligible current drain, battery life is likely to be determined by the frequency and duration of system testing, at which time the current is appoximately 0.3 milliamp. A suitable time for transistor 118 to reach a steady level of conduction is about 150 milliseconds. Operationally, the battery voltage (of a standard, small nine volt alkaline battery) is not critical. Dependent upon values of the resistors, the sensing function can be preserved at a drop of battery voltage down to about five volt. Further, the circuit will effect an output signal for any value of $R_x$, including a value significantly higher than that encountered in the event of a tiny pinhole in the membrane in the balloon 12 (50 to 100 Kohm).

Figure 9:
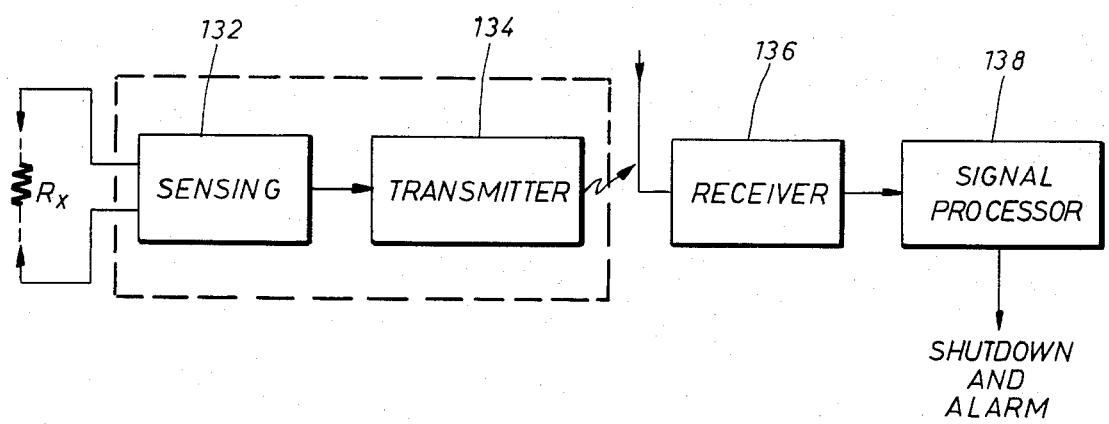
FIG. 9 is an electrical block diagram of a system for direct current sensing combined with telemetry.

Referring now to FIG. 9, a block diagram is shown of a system that includes telemetry, which, as noted, lends itself to an extension of the dc approach to balloon leak detection. Using a conventional design, a low powered transmitter section 134 may be combined with the sensing section 132 of FIG. 8 in a common battery powered unit for transmitting to a receiver 136 and to a signal processor 138 for effecting alarm and shutdown, as previously disclosed. Again, the current drain is negligible in the standby, non-triggered mode; and maximum electrical isolation from earth ground is inherent in this configuration.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts will be readily apparent to those skilled in the art and which are encompassed within the spirit of the invention and the scope of the appended claims.

What is claimed is:

1. An apparatus for monitoring the operation of an intra-aortic balloon inserted into the aorta of a body in which the balloon includes an electrical conductor therein for extending out of the body comprising,
    an intra-aortic balloon for inserting into the aorta of a body, said balloon including an electrically conductor therein for extending out of the body,
    an electrode affixed to the exterior of the body,
    an electrical current source connected to the electrode and to the electrical conductor, and
    an impedance measuring means electrically connected to the electrode and the electrical conductor for measuring the impedance of the balloon for monitoring its operation.

2. The apparatus of claim 1 including operating means for inflating and deflating the balloon and electrical shutdown means connected to the measuring means for automatically stopping the operation of the balloon when the impedance falls below a predetermined level.

3. The apparatus of claim 2 including signal producing means connected to the measuring means for actuating a second signal when the impedance exceeds a predetermined level.

4. The apparatus of claim 2 including means limiting the electrical current flowing between the electrode and the electrical conductor.

5. The apparatus of claim 4 wherein the current source is an alternating current source and the frequency of the alternating current is above ten KHZ.

6. The apparatus of claim 1 wherein the current source is a battery powered, constant current source for the detection of the electrical conductance across a defective balloon.

7. The apparatus of claim 6 wherein the conductance measuring means includes an optical transmission device.

8. An apparatus for monitoring the operation of and detecting a leak in an intra-aortic balloon inserted into the aorta of a body in which the balloon is inflated and deflated with gas by an electrical conductor therein extending out of the body comprising,
    an intra-aortic balloon for inserting into the aorta of a body, said balloon including an electrical conductor for extending out of the body,
    a gas control system connected to the balloon for inflating and deflating the balloon with gas,
    an electrode for connection to the exterior of the body,
    an electrical subassembly including an alternating current impedance measuring circuit connected to the electrode and the electrical conductor for providing a current path through the body across the balloon,
    a direct current power supply connected to the subassembly, said power supply being electrically isolated from earth ground and providing power to the measuring circuit,
    a sinusoidal oscillator providing an alternating current signal to the measuring circuit,
    a first transformer positioned between the oscillator and the measuring circuit,
    an alternating current to direct current converter connected to the output of the a control system and in which the balloon includes measuring circuit,
    a second transformer connected between the converter and the output of the measuring circuit,
    a signal processor connected to the output of the converter for providing an output proportional to the measured impedance, said output of the processor connected to the gas control system for deactivating the control system when the measured impedance falls below a predetermined level.

9. The apparatus of claim 8 wherein the impedance measuring circuit includes a current limiting means for limiting the current passing through the body.

10. The apparatus of claim 8 wherein the frequency output of the oscillator is higher than ten KHZ.

11. The apparatus of claim 8 wherein the signal processor includes first and second comparators for the generation of signals when measured impedance increases above a predetermined level and when the measured impedance decreases below a different predetermined level, respectively.

12. The apparatus of claim 11 including a latch actuated by the second comparator for deactivating the control system, said latch having a manual actuation for resetting.

13. The method of monitoring the operation of an intra-aortic balloon inserted into the aorta of a body in which the balloon includes an electrical conductor therein extending out of the body comprising,
    operating the balloon by inflating and deflating the balloon with gas,
    attaching the electrode to the exterior of the body,
    applying a current source between the electrical conductor and the external electrode providing a current path through the body across the balloon, and
    measuring the impedance between the electrical conductor and the electrode while the balloon is inflated and deflated thereby monitoring the expansion and contraction of the intact balloon and detecting any leaks in the balloon membrane.

14. The method of claim 13 including,
    shutting down the operation of the balloon when the impedance falls below a predetermined level.

15. The method of claim 14 including,
    generating a signal in response to the measured impedance and actuating a second signal when the impedance exceeds a predetermined level.

16. The method of claim 13 wherein the frequency of the alternating current is above the range of cardiac susceptibility.

17. The method of claim 13 including limiting the electrical current passing through the body.

18. The method of claim 13 including,
attaching a second electrode to the surface of the body, and connecting this electrode to a shunt resistor which is in parallel to the current path between the first electrode and the electrical conductor.

19. The method of detecting leaks in an intra-aortic balloon inserted into the aorta of a body in which the balloon is inflated and deflated with gas by a control system and in which the balloon includes an electrical conductor therein extending out of the body comprising,
attaching an electrode to the exterior surface of the body,
applying a direct current source between the electrical conductor and the electrode thereby transmitting a direct current through the body and across the fluid path in a defective balloon, and
measuring the change of conductance between the electrical conductor and the electrode which is an indication of any leak in the balloon.

* * * * *